United States Patent [19]

Cheng et al.

[11] Patent Number: 5,800,363
[45] Date of Patent: Sep. 1, 1998

[54] METHOD FOR DIAGNOSING AND MONITORING OSTEOPOROSIS

[76] Inventors: Shu Lin Cheng, 7927 Farnifold, #2, Germantown, Tenn. 38138; Jussi Timonen, Soidintie 5 C; Harri Suominen, Soidintie 1, #3, both of Fin-40630 Jyväskylä, Finland

[21] Appl. No.: 624,018

[22] Filed: Mar. 27, 1996

[51] Int. Cl.$^6$ ............................. A61B 5/103; A61B 19/00
[52] U.S. Cl. ............................................. 600/587; 600/553
[58] Field of Search ............................. 128/739, 740, 128/744, 782, 660.01, 660.03; 606/53, 1, 63

[56] References Cited

U.S. PATENT DOCUMENTS

| | | | |
|---|---|---|---|
| 4,235,243 | 11/1980 | Saha | 128/740 |
| 4,754,763 | 7/1988 | Doemland | 128/739 |
| 4,799,498 | 1/1989 | Collier | 128/739 X |
| 5,006,984 | 4/1991 | Steele | 128/744 X |
| 5,143,069 | 9/1992 | Kwon | 128/660.01 |
| 5,368,044 | 11/1994 | Cain | 128/739 |
| 5,402,781 | 4/1995 | Dimarogonas | 128/660.01 X |

OTHER PUBLICATIONS

Elastic Wave Propagation In Bone In Vivo: Methodology by Sulin Cheng et al., dated Apr., 1995, J. Biomechanics, vol. 28, No. 4, pp. 471–478.

*Primary Examiner*—Richard J. Apley
*Assistant Examiner*—William LaMarca
*Attorney, Agent, or Firm*—Fildes & Outland, P.C.

[57] ABSTRACT

A method for diagnosing and monitoring osteoporosis includes the steps of:

stimulating the tibia of a patient, to create a pulse that progresses in the bone, which can be registered as a function of time;

measuring accelerations of the pulse at at least two spaced locations, at an interval from the point of stimulation and at an interval from one another, as a temporal function, both measurement points being at a distance of at least 1/6 of the length of the tibia from its nearest end;

measuring the diameter of the bone to provide a quantity depicting the geometry of the bone, at a predetermined point on the tibia and estimating the density of the bone tissue at the same point, measuring the velocity V of a pulse in the bone to provide a quantity depicting the condition of the bone, over at least one measurement interval;

calculating at least one of the following factors over at least one measurement interval:
  a coefficient R, dependent on the variation of the bone tissue,
  a coefficient K, dependent on changes in the cross-sectional surface area of the bone, and
  a coefficient P, dependent on changes in the modulus of elasticity of the bone, and quantifying the condition of the bone tissue of the patient as a function of the quantities V and at least one of R/K/P.

10 Claims, 2 Drawing Sheets

METHOD FOR DIAGNOSING AND MONITORING OSTEOPOROSIS

FIELD OF THE INVENTION

This invention relates to a method for diagnosing and monitoring osteoporosis.

BACKGROUND OF THE INVENTION

Osteoporosis, the increase in the brittleness of bones, is a health problem of aging people—particularly women. Osteoporotic fractures and the complications associated with them have caused a significant increase in health care costs as the age structure of the population grows older.

Osteoporosis has generally been investigated by examining the mineral content and/or density of bones. Generally it is not possible to determine the real density of bones by conventional methods. These methods include periodic X-ray imaging, photon absorption and computed tomography, none of which can provide detailed information about the mechanical properties of bone, such as elasticity and strength. In fact, the loss with age of the biomechanical strength of bone is more pronounced than the loss of bone mass, and, at any given age, there is greater inter-individual variation in the mechanical properties of bone than in the bone mass. Therefore, it is desirable to develop a clinically relevant method for determining the mechanical properties of bone. Additional drawbacks of the methods are radiation-predisposition caused by exposure to ionizing radiation and considerable equipment costs.

Measurements of bone density do not, as such, provide sufficient information on the various properties of bones. In particular, reliable information on the fracture sensitivity of a bone cannot be obtained.

SUMMARY OF THE INVENTION

An object of this invention is to provide a method for the evaluation of the geometrical and mechanical properties of bones and more particularly to provide a new simple method of measuring the structure and strength of a skeleton that is safe for the patient.

In accordance with the method, measurements are made of the velocity of bending waves in the tibia of the patient. These are used to calculate various indices, which give a better picture of the osteoporotic condition of the patient's skeleton.

According to the method for diagnosing and monitoring osteoporosis, a stimulus is directed onto the tibia of the patient, which creates a pulse that progresses in the bone, which is registered as a function of time, the accelerations are measured at two places, at an interval from the point of stimulation and at an interval from one another, as a temporal function, both measurement points being at a distance of at least ⅙ of the length of the tibia from its nearest end, a quantity depicting the geometry of the bone, for example the diameter, is measured at a predetermined point on the tibia and an estimate is made of the density of the bone tissue at the same point, a quantity depicting the condition of the bone, for example the velocity V of a pulse in the bone, is measured over at least one measurement interval, at least one of the following factors is measured over at least one interval:

coefficient R, which depends on the variation of the bone tissue, coefficient K, which depends on changes in the cross-sectional surface area of the bone, coefficient P, which depends on changes in the modulus of elasticity, and the quantities V and R/K/P are used to evaluate the condition of the bone tissue of the patient.

A computer tomography picture is taken of the bone at at least one cross-sectional point. From the picture, the proportional quantities of the outer and inner diameter of the bone are calculated. In addition the proportional quantity of the density of the bone at the cross-sectional point in question is also calculated. Alternatively an X-ray picture can be taken of the bone at at least one cross-sectional point and the average density of the bone tissue calculated from the x-ray picture.

The stimulus can be generated by a mechanical hammer, the force of impact of which is measured electrically by means of a strain gauge. The analog signal of the strain gauge is converted into a digital signal and transferred to a computer. Alternatively the pulse progressing through the bone can be generated by means of an ultrasound transmitter. The accelerations are measured electrically with by means of piezoelectric sensors with the analog signals obtained being converted to digital signals and transferred to a computer.

Preferably the point of application of the stimulus is generally a distance from the end of the tibia equalling 0.05–0.15 times the entire length of the tibia. Furthermore the points of measurement of the accelerations are generally a distance from the point of stimulation that one is 0.20–0.40 and the other 0.40–0.60 times the entire length of the tibia and their mutual interval is 0.1–0.3 times the entire length of the tibia.

In another method, the coefficients R, K and P are measured over two spaced intervals and these quantities are used to indicate the condition of the bone tissue of the patient.

Although this diagnostic method does not eliminate radiation-predisposition, it permits the amount to be significantly reduced. The method provides useful additional information for density measurements and computer tomography examinations.

The method provides data on different kinds of parts of a bone (intervals F-A and A-B). By selecting the minima of two quantities, besides velocity V, for example $P_{F-A}$ and $K_{A-B}$, a much more accurate picture of the properties of the patient's bone can be obtained.

These and other features and advantages of the invention will be more fully understood from the following detailed description of the invention taken together with the accompanying drawings.

DETAILED DESCRIPTION OF THE INVENTION

Subjects were selected from a population of 78-year-old women living in the city of Jyväskylä according to their bone mineral density (BMD) previously measured at the calcaneus by the I-photon absorption method. A letter was sent to 22 women selected randomly from those with BMD$\geq$0.160 g·cm$^{-3}$ (group I) and to 23 women with BMD<0.100 g·cm$^{-3}$ (group II). Two subjects refused, 2 were ill during the tests, 4 failed to show up and bone measurements were not obtained for 1 person. The high BMD group thus comprised 19 and the low BMD group 17 subjects. 5 (26%) of the subjects in group I and 12 (71%) of the subjects in group II had fractured a bone at least once after the age of 50. All the subjects in the group II had calcaneus BMD values below the fracture threshold. The fractured bone sites were mainly at metacarpi, upper arm and lower leg or ankle.

Figure 1:
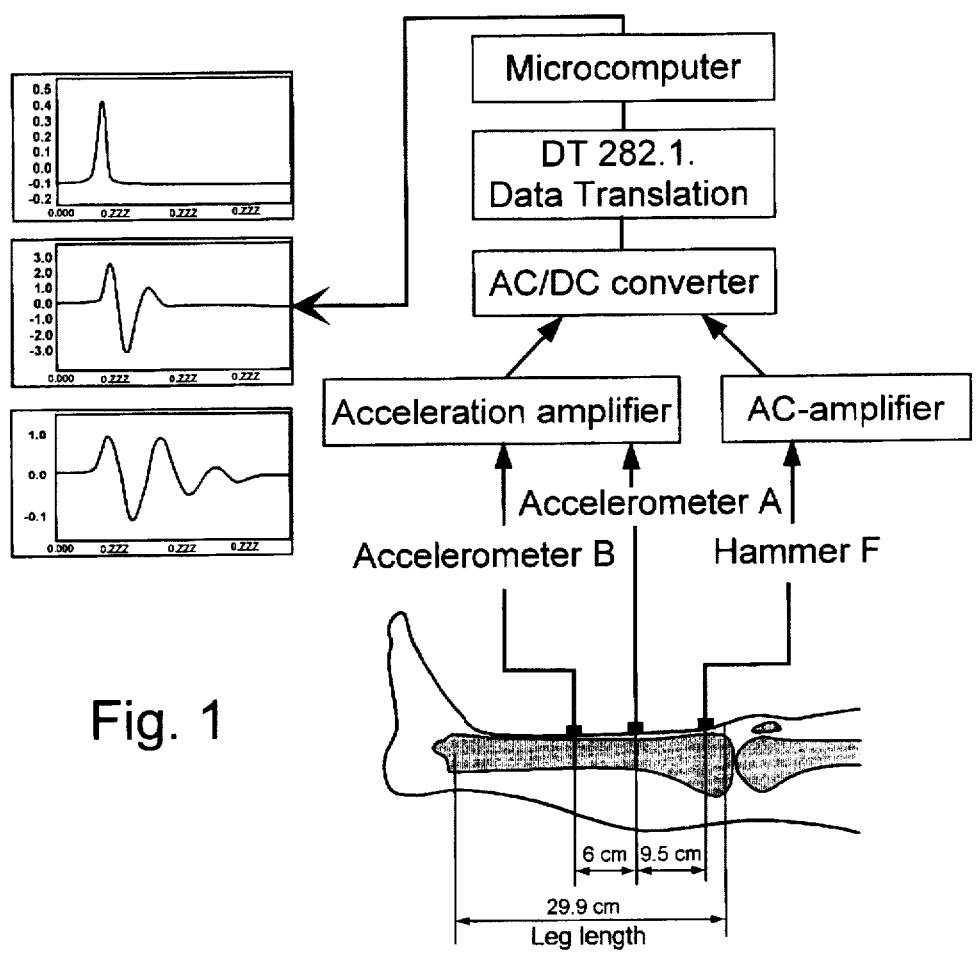
FIG. 1 is a schematic presentation of the points used for the hammer strike and two accelerometers (A and B) on the tibia surfaces together with an example of recorded signals, the upper trace shows the impact force, and middle and lower traces show the response of the two accelerometers.

Elastic wave propagation (EWP) measurements in vivo were performed on the right tibia as illustrated in FIG. 1. The EWP apparatus comprised a hammer F with a force strain gauge which produced the impact (natural frequency 10 kHz), and two accelerometers A, B (Brüel and Kjær, weight 11 g, Type 4371) adjusted to a pre-spring mass load of 3N and placed on the leg. The pre-spring mass load on the accelerometers was kept constant by mounting a piece of sponge between the pre-spring mass load and the accelerometer. The distances (L) between the hammer (F) and the two accelerometers A and B were always such that $$L_{F-A}=L_{leg} \cdot 0.33, \text{ and } L_{F-B}=L_{leg} \cdot 0.53$$

The experimental arrangement was such that the subject sat on a chair with the subcutaneous surface of the tibia placed horizontally on a table. The preselected points for the hammer strike and for the accelerometer contacts were determined on the skin surface. The accelerometers A and B were positioned on the tibia distal at the prescribed distances from the point of the hammer strike. The hammer was dropped from a fixed height of 4 cm on to the tibia tubercular. The force and acceleration outputs were collected simultaneously by using a DT 2821 Data Translation software package (sampling frequency 40 kHz per channel). The velocity of the pulse of mainly bending waves produced by the hammer was calculated from the measured signals using calibrated time intervals determined from the first detected peaks of the acceleration curves (F to A and A to B) and from the known distances between the three points.

Figure 2:
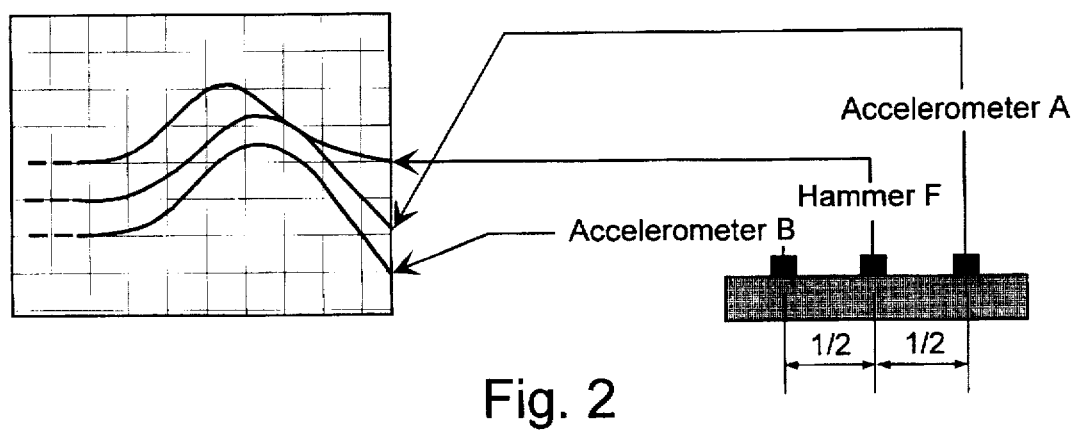
FIG. 2 is a schematic presentation of the timing accuracy of the diagnosing equipment as tested on nylon and acrylic rods, the upper trace shows the impact force, and middle and lower trances show the response of the two accelerometers (horizontal scale is 200 µs)
Figure 3:
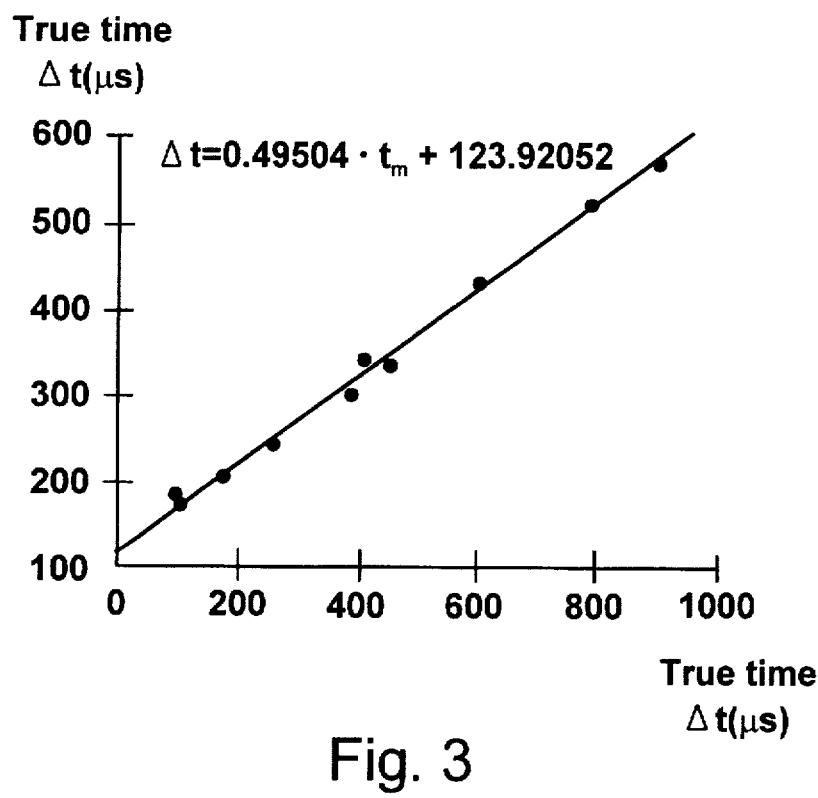
FIG. 3 is a graphic representation of calibration of the measured time intervals for nylon and acrylic rods.

The timing accuracy of the apparatus was tested on nylon and acrylic rods (D=50 mm), and found to be ±16 μs as illustrated in FIG. 2. The results for nylon and acrylic were also used for calibrating the measured time intervals illustrated in FIG. 3 in order to exclude the effect of the apparent slowing of a pulse of bending waves caused by dispersion. It was found that the slowing of the pulse was directly proportional to the recording distance. The reproducibility of the measured velocities was tested on nylon and acrylic rods as well as on human tibia. The coefficient of variation (CV) ranged from 0.001% to 0.9% for nylon and acrylic, and from 2.5% to 4.8% for human tibia.

A computerized tomographic (CT) scanner (Siemens SOMATOM CR) was used to determine the bone density and cross-sectional area (CSA) at the same (intersection) points as the velocity measurements. The system parameters employed were as follows: pixel size at X and Y of 0.2 mm, a slice thickness of 2 mm, the pixel matrix of 256×256, and exposure factors of 125 kV, 500 mA and 7 s. Simulated bone standards, i.e. known concentrations of $K_2HPO_4$ in plastic containers were used to determine the relationship between the attenuation coefficient μ (HU) and the density ρ (g·cm$^{-3}$)

A piece of frozen cow bone with soft tissues corresponding to human tibia was also used as a standard in the CT scanner for determining the bone density. Ash density was calculated as ash weight/sample volume. The ash density was found to be 7.6% higher than the CT density as determined on the basis of the attenuation in $K_2HPO_4$. This result was subsequently used to adjust the density produced by the CT method. The reproducibility of the CT density (HU) averaged 3.2% for the $K_2HPO_4$, and 3.0% for the cow bone.

The coefficient of variation between repeated measurements was 1.4% for the outer CSA and 4.9% for the inner CSA of the bone. The CSA of the cow bone was also measured directly (Summagraphics 10, Data Tablet/Digitizer, Fairfield, USA). The directly measured CSA was found to be 5.4% smaller than the CT-CSA.

The dramatic change in the geometry of the upper part of the tibia immediately below the knee joint makes it difficult to interpret there the velocity of a pulse of bending waves. However, further down from the knee joint it is reasonable to assume a piecewise linear variation with distance for the geometrical (and also other) properties of bone. Moreover, results for solid and hollow rods of various plastics illustrate that a linear calibration of the measured time interval provides a constant reproducible velocity for the pulses produced by a mechanical hammer. Therefore velocity found in this way is locally given by that of the elementary theory of bending waves, which for a homogeneous rod of constant cross-sectional area A is $$V=C\lambda^{-1}(YI/\rho A)^{1/2},$$

where C is a numerical factor, λ is the wave length of the mode, Y is Young's modulus and I is the area moment of inertia for the cross section of the rod. For hollow rods A means $A_2-A_1$, $A_2$ being the outer cross-sectional area and $A_1$ the cross-sectional area of the hollow core.

The measured velocities also depend on how bone density and bone geometry change along the length of bone under scrutiny. In order to extract from the velocities the mechanical and elastic properties of bone, changes in the density and geometry of bone are taken into account. Away from the immediate vicinity of the bone joint there is a piecewise linear dependence of these quantities relative to the distance along the bone. By using this relationship it is possible to calculate the average velocities over a given distance and three quantities or coefficients, R, K and P hereinbelow defined, which can be used as indicators of the mechanical and elastic properties of bone.

By increasing the density of the mesh which divides the bone into pieces within which simple linear dependence is assumed, this procedure can be made arbitrarily accurate independent of the actual change of the considered quantities along the whole measured distance. For analytical convenience, i.e. for being able to use analytical expressions instead of a numerical procedure, it is sufficient to use only one or two mesh points in this division into pieces with simple linear dependence.

A "mass dependence" is extracted from the measured velocity by considering the quantity R which is a combination of (average values of) Young's modulus and the area moment of inertia. The quantity R is expressed as $$R = \sqrt{E} \cdot \frac{<V>_{measured}}{<V>_{calculated}},$$

wherein E stands for a combination of numerical constants including Young's modulus, the moment of inertia and wave length. In actuality some of these factors will also change along the bone.

The quantity, K, also includes the change along the bone in the area moment of inertia. The velocity of bending waves in circular cylinders (cross-sectional area $A_2$) with a hollow inner core along the central axis (cross-sectional area $A_1$) being proportional to $[\rho^{-1}(A_1+A_2)]^{1/2}$ allows velocity V to be expressed as $$V = K\sqrt{\frac{1}{\rho}(A_1 + A_2)},$$

where K represents the other factors which enter the expression, the most important being Young's modulus. Coefficient K is thus a measure of the average value of Young's modulus.

Figure 4:
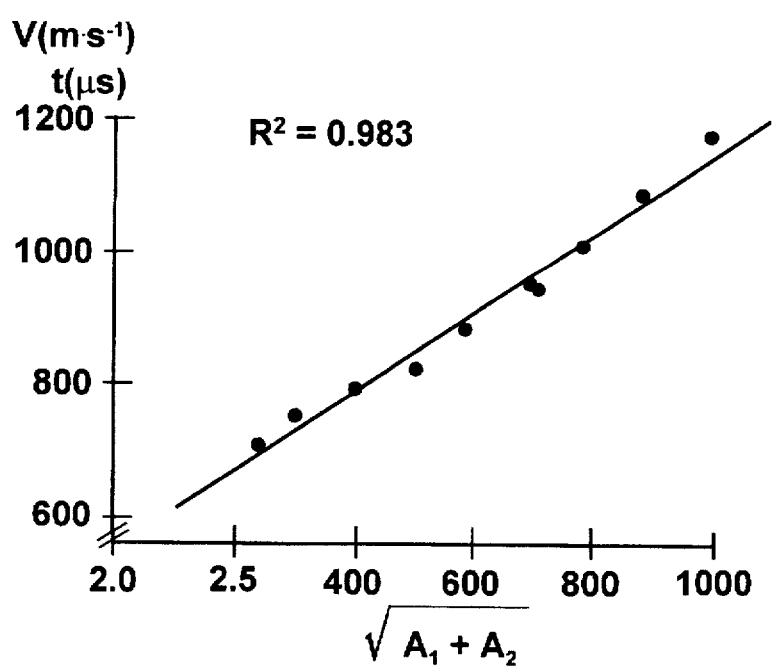
FIG. 4 is a graphic representation of the velocity of elastic waves vs square root of the inner CSA plus outer CSA in PVC tubes.

The relationship $$V \propto \sqrt{A_1 + A_2}$$

was tested for Poly Vinyl Chloride (PVC, density 1.4 g·cm$^{-3}$) tubes of varying inner and outer diameters. The results of these measurements is illustrated in FIG. 4.

In order to also include the effect of changes in the Young's modulus Y, an assumption concerning its dependence, e.g. on bone density, has to be made. The quantity P is based on the assumption $Y \propto \rho^2$ so that a calculation similar to the one which leads to the definition of K above now yields a similar expression for P. The value of P remains virtually constant along the length of bone.

An attenuation coefficient $\alpha$ of the elastic wave propagation of the tibia is expressed as $$\alpha = \frac{1}{L_{a-b}} \ln\left(\frac{\epsilon_1}{\epsilon_2}\right)$$

where $\epsilon_1$ and $\epsilon_2$ are the peak amplitudes at points A and B along the bone, and $L_{A-B}$ is the distance between A and B.

The significance of the differences between the two groups of subjects was determined by the Students t-test (two-tailed).

Bone mineral densities, measured velocities, and the R, K and P coefficients of the tibia as defined above are shown in Table 1. Group I had a significantly higher BMD value than group II at the three selected sections. Measured velocity decreased with increases in the measuring distance, and the magnitude of this effect was found to be different in the two groups. In group I, velocity was lower in F-A and higher in A-B than in group II. In group I there was a 53% decrease, and in group II, a 66% decrease from F-A to A-B in average velocity. Meanwhile, density changed by only 31% from F to A and by 6% from A to B in group I, and by 33% and by 6%, respectively, in group II. In coefficient R, which incorporates the effect of changing mass, the change from F-A to A-B was 54% in group I, and 68% in group II. In coefficient K, which also includes the change in the area moment of inertia, there was a significant difference between the two groups in $K_{A-B}$, but not in $K_{F-A}$. In coefficient P, which includes the changes in density, Young's modulus and area moment of inertia, the difference between the two groups disappeared as measured from the interval A-B. It should be noted that for group I in particular, coefficient P remains constant along the bone, thus indicating the inclusion of all the relevant factors in the definition of P. Furthermore, the attenuation of the elastic waves was different in the two groups ($\alpha=0.047\pm0.041$ in group I and $\alpha=0.081\pm0.050$ in group II, p=0.056).

TABLE 1

Tibia bone mineral density (BMD), average velocity of elastic wave (V) and R, K and P coefficients in groups of high (group I) and low (group II) BMD of 78-year-old women (Mean ± SD)

| Variable | Bone Section | Group I (n = 14) | Group II (n = 16) | p |
|---|---|---|---|---|
| BMD | F-section | 0.754 ± 0.093 | 0.612 ± 0.088 | <0.001 |
| (g · cm$^3$) | A-section | 1.086 ± 0.043 | 0.911 ± 0.108 | <0.001 |
| | B-section | 1.150 ± 0.045 | 0.973 ± 0.120 | <0.001 |
| V(m · s$^{-1}$) | F-A | 348 ± 46 | 417 ± 80 | 0.007 |
| | A-B | 164 ± 31 | 143 ± 20 | 0.030 |
| R | F-A | 7.61 ± 2.52 | 8.94 ± 2.18 | 0.132 |
| (10$^4$ g$^{1/2}$cm$^{1/2}$s$^{-1}$) | A-B | 3.48 ± 0.72 | 2.83 ± 0.54 | 0.009 |
| K | F-A | 1.22 ± 0.38 | 1.30 ± 0.23 | 0.457 |
| (10$^4$ g$^{1/2}$cm$^{-3/2}$s$^{-1}$) | A-B | 6.00 ± 0.79 | 4.71 ± 1.21 | 0.002 |
| P | F-A | 1.20 ± 0.37 | 1.54 ± 0.23 | 0.005 |
| (10$^4$ g$^{1/2}$cm$^{3/2}$s$^{-1}$) | A-B | 1.17 ± 0.18 | 1.19 ± 0.51 | 0.854 |

The relationship between bone loss and decrease in the velocity of elastic waves, is related to the osteoporosis index. Typically the aging processes changes the properties of bone such that a decrease in the velocity of elastic waves occurs with increased age. In this case when the initial pulse was produced by hammer F, the excited modes are to the most part bending waves for both solid and hollow plastic rods.

Between points F and A, the changes in bone geometry and bone structure as well as the ratio between cortical and trabecular bone are quite dramatic, and thus more detailed analysis is needed to draw definite conclusions from $<V>_{F-A}$. Therefore, we are more concerned here with the results for the middle part (A-B) of the tibia, although we can qualitatively explain the variations in the observed velocities between the two groups and the two pieces of bone.

It was difficult to name a unique factor which would explain this behavior of the velocity as there are many factors which come into play. We analyzed the roles of various quantities in determining the observed velocity via the coefficients R, K and P.

Coefficient R includes the effect of changes in the bone mass in the form in which it explicitly appears in the theoretical velocity of elastic waves. It therefore includes the effects of elastic constants and bone geometry (area moment of inertia) in an averaged way. The results shown in Table 1 indicate that these two quantities are important factors in determining the observed velocity.

Coefficient K includes changes along the bone in both density and area moment of inertia. Again it seems that there was a significant difference in velocity $<V>_{A-B}$ between the two groups. The big change in the value of K along the bone in both groups arises from the changing elastic constants (Young's modulus).

It is not quite clear how to include the changing elastic constants in factor P. Assuming that these other factors have only little effect on the observed trend, it is reasonable to conclude that Young's modulus is a function of bone density such that it increases with density at a greater than linear rate. In a qualitative analysis it is not of overwhelming importance to know precisely the exact degree of dependence, and therefore in our definition of factor P Young's modulus is proportional to density squared. The results given in Table 1 seem to lend support to the qualitative correctness of our assumptions in the way that P remains roughly constant along the bone (in both groups). The changes in the velocity along the bone and the differences between the two groups as given in Table 1, are qualitatively explained by the changes in bone density, area moment of inertia and density dependent Young's modulus. This means that the average value, for each distance, of the quantity $\sqrt{\pi(A_1+A_2)}$ behaves in the same way as the observed velocity.

Variations in velocity along the bone are sensitive enough to be used in estimating the changes in the mechanical properties of bone in the elderly.

It is important to specify the section of the bone over which the velocity is measured. Useful information may be obtained by comparing the changes along the bone in the measured velocities. The experimental set-up is such that the measured velocity is that of a pulse of bending waves. This velocity is usually much lower than that of longitudinal elastic waves. The measured velocities in both groups are very low in comparison with those found for young individuals and, therefore, considerable changes in the mechanical properties of bone must have taken place in both groups, particularly in group II (low density).

The changes in the velocities of bending waves can be explained by changes in bone density and cross-sectional area. In isolating the effect of bone density it is important to include its effect on the elastic constants of bone such as Young's modulus. Thereby the factors R, K and P combined with the measured velocities of elastic waves generated in the tibia can be used as indicators of the mechanical properties of the patient's bone.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A method for diagnosing and monitoring osteoporosis characterized by the steps of:

stimulating the tibia of a patient, to create a pulse that progresses in the bone, which can be registered as a function of time;

measuring the velocity of the pulse at at least two spaced locations, at an interval from the point of stimulation and at an interval from one another, as a temporal function, both measurement points being at a distance of at least 1/6 of the length of the tibia from its nearest end;

measuring the diameter of the bone to provide a quantity depicting the geometry of the bone, at a predetermined point on the tibia, measuring the density of the bone tissue at the same point;

calculating, based on measured velocity, bone diameter and bone tissue density, at least one of the following factors over at least one measurement interval;
   a coefficient R, dependent on the variation of the bone tissue over the distance measured,
   a coefficient K, dependent on changes in the cross-sectional surface area of the bone over the distance measured, and
   a coefficient P, dependent on changes in the modulus of elasticity of the bone over the distance measured; and quantifying the condition of the bone tissue of the patient as a function of the quantities V and at least one of R/K/P/.

2. The method of claim 1 characterized by calculating the proportional quantities of the outer and inner diameter of the bone using a computer tomography picture taken of the bone at at least one cross-sectional location along the bone.

3. The method of claim 2 characterized by calculating the proportional quantity of the density of the bone at the cross-sectional point in question from the computer tomography picture.

4. The method of claim 1 characterized by calculating the average density of the bone tissue using an X-ray picture taken of the bone at at least one cross-sectional point.

5. The method of claim 1 characterized in that stimulating the tibia is performed by a mechanical hammer, the force of impact being measured electrically by means of a strain gauge and the analog signal obtained is converted into a digital signal and transferred to a computer.

6. The method of claim 1 characterized in that stimulating the tibia is performed by means of an ultrasound transmitter.

7. The method of claim 1 characterized in that the accelerations are measured electrically by means of piezoelectric sensors and the analog signals obtained are converted to digital signals and transferred to a computer.

8. The method of claim 1 characterized in that stimulating the tibia is performed a distance from the end of the tibia generally in the range of 0.05–0.15 times the length of the tibia.

9. The method of claim 1 characterized in that the accelerations are measured a distance from the point of stimulation such that one is generally 0.20–0.40 and the other being generally 0.40–0.60 times the entire length of the tibia and their mutual interval being generally 0.1–0.3 times the entire length of the tibia.

10. The method of claim 1 characterized by measuring velocity V and the coefficients R/K/P over at least two intervals and quantifying these quantities to indicate the condition of the bone tissue of the patient.

* * * * *